(12) United States Patent
Schembri

(10) Patent No.: US 6,887,715 B2
(45) Date of Patent: May 3, 2005

(54) METHODS AND COMPOSITIONS FOR PRODUCING BIOPOLYMERIC ARRAYS

(75) Inventor: Carol T. Schembri, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 223 days.

(21) Appl. No.: 09/997,564

(22) Filed: Nov. 28, 2001

(65) Prior Publication Data

US 2002/0072128 A1 Jun. 13, 2002

Related U.S. Application Data

(62) Division of application No. 09/354,816, filed on Jul. 16, 1999, now Pat. No. 6,346,423.

(51) Int. Cl.⁷ .................... G01N 33/543; C12M 3/00
(52) U.S. Cl. .................... 436/518; 436/501; 435/287.1; 435/287.2; 435/287.3
(58) Field of Search .................... 435/4, 7.1, 287.1, 435/287.2, 287.3; 436/518, 501

(56) References Cited

U.S. PATENT DOCUMENTS

| | | | |
|---|---|---|---|
| 4,415,732 A | 11/1983 | Caruthers et al. | |
| 4,877,745 A | 10/1989 | Hayes et al. | |
| 5,143,854 A | 9/1992 | Pirrung et al. | |
| 5,242,974 A | 9/1993 | Holmes | |
| 5,338,688 A | 8/1994 | Deeg et al. | |
| 5,384,261 A | 1/1995 | Winkler et al. | |
| 5,405,783 A | 4/1995 | Pirrung et al. | |
| 5,412,087 A | 5/1995 | McGall et al. | |
| 5,424,186 A | 6/1995 | Fodor et al. | |
| 5,429,807 A | 7/1995 | Matson et al. | |
| 5,436,327 A | 7/1995 | Southern et al. | |
| 5,445,934 A | 8/1995 | Fodor et al. | |
| 5,449,754 A | 9/1995 | Nishioka | |
| 5,472,672 A | 12/1995 | Brennan | |
| 5,474,796 A | 12/1995 | Brennan | |
| 5,491,097 A * | 2/1996 | Ribi et al. .................. 436/518 |
| 5,510,270 A | 4/1996 | Fodor et al. | |
| 5,527,681 A | 6/1996 | Holmes | |
| 5,529,756 A | 6/1996 | Brennan | |
| 5,532,128 A | 7/1996 | Eggers et al. | |
| 5,545,531 A | 8/1996 | Rava et al. | |
| 5,552,270 A | 9/1996 | Khrapko et al. | |
| 5,554,501 A | 9/1996 | Coassin et al. | |
| 5,556,752 A | 9/1996 | Lockhart et al. | |
| 5,561,071 A | 10/1996 | Hollenberg et al. | |
| 5,599,695 A | 2/1997 | Pease et al. | |
| 5,605,662 A * | 2/1997 | Heller et al. .................. 422/68.1 |
| 5,624,711 A | 4/1997 | Sundberg et al. | |
| 5,639,603 A | 6/1997 | Dower et al. | |
| 5,653,939 A * | 8/1997 | Hollis et al. .................. 422/50 |
| 5,658,734 A | 8/1997 | Brock et al. | |
| 5,658,802 A | 8/1997 | Hayes et al. | |
| 5,670,322 A | 9/1997 | Eggers et al. | |
| 5,677,195 A | 10/1997 | Winkler et al. | |
| 5,698,089 A | 12/1997 | Lewis et al. | |
| 5,700,637 A | 12/1997 | Southern | |
| 5,723,320 A | 3/1998 | Dehlinger | |
| 5,744,305 A | 4/1998 | Fodor et al. | |
| 5,759,779 A | 6/1998 | Dehlinger | |
| 5,763,170 A | 6/1998 | Raybuck | |
| 5,846,708 A | 12/1998 | Hollis et al. | |
| 6,346,423 B1 * | 2/2002 | Schembri .................... 436/518 |

FOREIGN PATENT DOCUMENTS

| | | |
|---|---|---|
| EP | 0 373 203 | 8/1994 |
| EP | 0 742 287 | 11/1996 |
| EP | 0 799 897 | 10/1997 |
| WO | WO 90/10716 | 9/1990 |
| WO | WO 92/10588 | 6/1992 |
| WO | WO 93/17126 | 9/1993 |
| WO | WO 95/11995 | 5/1995 |
| WO | WO 95/35505 | 12/1995 |
| WO | WO 97/10365 | 3/1997 |
| WO | WO 97/27317 | 7/1997 |
| WO | WO 97/46313 | 12/1997 |
| WO | WO 98/01758 | 1/1998 |

* cited by examiner

*Primary Examiner*—Padmashri Ponnaluri
*Assistant Examiner*—My-Chau T Tran

(57) ABSTRACT

Methods and compositions are provided for producing arrays of polymeric binding agents. In the subject methods, the individual polymers of the array are synthesized using solid phase synthesis techniques on the surface of a substrate. A critical feature of the invention is that one or more locations on the substrate surface are spatially and temporally protected by a protective bubble during the synthesis protocol, where the protective bubble may be produced using any convenient bubble producing means. The bubble producing means may be a component of either a substrate or a structure separate from the substrate. Also provided are the arrays produced by the subject methods, kits for use in practicing the subject methods, and methods of using the arrays in analyte detection assays, including hybridization assays, such as gene discovery, differential gene expression and gene sequencing assays.

8 Claims, No Drawings

METHODS AND COMPOSITIONS FOR PRODUCING BIOPOLYMERIC ARRAYS

CROSS REFERENCE TO RELATED APPLICATION(S)

This is a divisional of application Ser. No. 09/354,816 filed on Jul. 16, 1999 now U.S. Pat. No. 6,346,423.

TECHNICAL FIELD

The field of this invention is polymeric arrays.

BACKGROUND OF THE INVENTION

"Biochips" or arrays of binding agents, such as oligonucleotides and peptides, have become an increasingly important tool in the biotechnology industry and related fields. These binding agent arrays, in which a plurality of binding agents are present on a solid support surface in the form of an array or pattern, find use in a variety of applications, including gene expression analysis, drug screening, nucleic acid sequencing, mutation analysis, and the like.

Such arrays may be prepared in a number of different ways. For example, DNA arrays may be prepared manually by spotting DNA onto the surface of a substrate with a micro pipette. See Khrapko et al., DNA Sequence (1991) 1:375–388. Alternatively, the dot-blot approach, as well as the derivative slot-blot approach, may be employed in which a vacuum manifold transfers aqueous DNA samples from a plurality of wells to a substrate surface. In yet another method of producing arrays of biopolymeric molecules, a pin is dipped into a fluid sample of the biopolymeric compound and then contacted with the substrate surface. By using a plurality or array of pins, one can transfer a plurality of samples to the substrate surface at the same time. Alternatively, an array of capillaries can be used to produce biopolymeric arrays. See WO 95/35505. In another method of producing biopolymeric arrays, arrays of biopolymeric agents are "grown" on the surface of a substrate in discreet regions. See e.g. U.S. Pat. No. 5,143,854 and Fodor et al., Science (1991) 251:767–773.

Despite the variety of different methods available for the production of biopolymeric arrays, there are disadvantages associated with each method. For example, current methods of growing the polymeric agents on the surface of an array, such as the photoresist techniques described in Fodor supra, are expensive and require the use of specialized photosensitive protecting groups on the phosphoramidites. As such, there is continued interest in the development of new methods for producing polymeric arrays, particularly in the development of new methods for growing polymers on the surface of a substrate to produce an array.

Relevant Literature

Patents and patent applications describing arrays of biopolymeric compounds and methods for their fabrication and/or use include: U.S. Pat. Nos. 4,877,745; 5,143,854; 5,242,974; 5,338,688; 5,384,261; 5,405,783; 5,412,087; 5,424,186; 5,429,807; 5,436,327; 5,445,934;5,449,754; 5,472,672; 5,474,796; 5,510,270; 5,527,681; 5,529,756; 5,532,128; 5,545,531; 5,552,270; 5,554,501; 5,556,752; 5,658,802; 5,561,071; 5,599,695; 5,624,711; 5,639,603; 5,658,734; 5,670,322; 5,677,195; 5,698,089; 5,700,637; 5,723,320; 5,744,305; 5,759,779; 5,763,170; 5,846,708; WO 90/10716; WO 92/10588; WO 93/17126; WO 95/11995; WO 95/35505; WO 97/10365; WO 97/27317; WO 97/46313; EP 0 373 203 B1; EP 742 287 A2; and EP 799 897 A1.

SUMMARY OF THE INVENTION

Methods and compositions for making polymeric arrays are provided. In the subject methods, polymers are produced through the sequential covalent addition of polymeric subunits to a growing polymer chain on the surface of a substrate, where one or more locations of the substrate surface are selective protected (both spatially and temporally) by a protective bubble during the sequential synthesis protocol. The protective bubble may be produced on the surface in any convenient manner, including through activation of bubble producing means, e.g. resistors, stably associated with a surface of the substrate or part of a structure separate from the substrate. A variety of different types of polymeric arrays can be produced according to the subject methods, including polypeptide and nucleic acid arrays. The subject arrays find use in a variety of different analyte detection applications, including hybridization assays, where specific applications include gene discovery, differential expression and nucleic acid sequencing assays.

Definitions

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to up to about 100 nucleotides in length.

The term "polynucleotide" as used herein refers to a single or double stranded polymer composed of nucleotide monomers of generally greater than 100 nucleotides in length and up to about 8,000 or more nucleotides in length.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "array" as used herein means an substrate having a plurality of binding agents stably attached to its surface, where the binding agents may be spatially located across the surface of the substrate in any of a number of different patterns.

The term "binding agent" means any agent that is a member of a specific binding pair, where such agents include: peptides, e.g. proteins or fragments thereof; nucleic acids, e.g. oligonucleotides, polynucleotides; and the like; etc.

DESCRIPTION OF THE SPECIFIC EMBODIMENTS

Methods and compositions are provided for producing arrays of polymeric binding agents. In the subject methods, the individual polymers of the array are synthesized using solid phase synthesis techniques on the surface of a substrate. A critical feature of the invention is that one or more locations on the substrate surface are spatially and temporally protected by a protective bubble during the synthesis protocol, where the protective bubble may be produced using any convenient bubble producing means. The bubble producing means may be a component of either a substrate or a structure separate from the substrate. Also provided are the arrays produced by the subject methods, kits for use in practicing the subject methods, and methods of using the arrays in analyte detection assays, including hybridization assays, such as gene discovery, differential gene expression and gene sequencing assays.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The subject invention provides methods for fabricating arrays of polymeric agents. The subject invention can be used to fabricate a number of different types of arrays in which a plurality of distinct polymeric binding agents are stably associated with at least one surface of a substrate. The polymeric binding agents may vary widely, where the only limitation is that the polymeric binding agents are capable of being fabricated in a step-wise fashion in which sub-units of the polymer, e.g. monomeric units, submonomers, macromonomers (i.e. compounds of two or more, usually no more than 10 and more usually no more than 8 monomers), are sequentially added to each other to form a growing polymeric chain to ultimately produce a polymeric molecule. Polymeric binding agents of particular interest include biopolymeric molecules, such as peptides, nucleic acids, polysaccharides and the like, where peptides and nucleic acids are of particular interest in many embodiments.

A critical feature of the subject methods is that protective bubbles are positioned on the surface of the substrate both spatially and temporally during the synthesis protocol in order to control the nature (i.e. sequence) of the polymers that are produced on the substrate surface. By spatially is meant that the location of the protective bubble(s) is selected in a specific manner, such that the protective bubble protects discrete and defined locations on the support surface during polymer synthesis. By temporally is meant that the duration and life of the protective bubble is selected such that a location on the substrate surface may be protected at one stage during synthesis and not protected at a second stage during synthesis. By modulating the location of the protective bubbles on the surface of the substrate during synthesis, arrays of polymers of defined sequence and location are produced.

The substrate surface may be protected with protective bubbles using any convenient means. Generally, a protective bubble producing means is employed to produce the protective bubble(s) that selectively protect one or more locations of the substrate surface at a given time during polymer synthesis. Although any type of bubble producing means that is capable of being activated to produce a bubble in a solvent layer positioned above the surface of the substrate during polymer synthesis may be employed, the bubble producing means is generally a heating means. In many embodiments, the heating means is a resistor. For convenience, the subject invention is now further described in terms of these embodiments in which the bubble producing means is a resistor.

The protective bubble producing means employed to produce the protective bubble(s) may incorporated into either the substrate or a structure separate from the substrate, with the only requirement being that the bubble producing means must be capable of protecting the substrate surface at the desired location and time during the synthesis process. Thus, in a first embodiment of the invention, the bubble producing means is a component of the substrate on which the polymers are grown, e.g. resistors are components of the substrate, as described in greater detail below. In a second embodiment, the bubble producing means (e.g. resistor) is a component of a structure separate from the substrate, such as a second plate that is brought into sufficient proximity of the substrate surface during synthesis, as described in greater detail below.

The substrate employed in the subject invention may be any convenient configuration, but generally has a planar configuration. By "planar configuration" is meant that the substrate has at least one planar surface, which surface may have any convenient cross-sectional shape, including circular, oval, square, rectangular and the like. In many embodiments, the substrate has a plate-like configuration, such as is found in a disk, rectangular slide, square slide, and the like. In many embodiments in which the ultimate array is to have a planar configuration, the substrate comprises at least one planar surface that has a cross-sectional area of at least about 4 mm$^2$, usually at least about 16 mm$^2$ and more usually at least about 25 mm$^2$, where the cross-sectional area of the planar surface may be as large as 2500 mm$^2$ or larger, but generally does not exceed about 900 mm$^2$ and usually does not exceed about 400 mm$^2$. In those embodiments where the planar surface has a square or rectangular shape, the planar surface has a length of from about 2 to 50 mm, usually from about 4 to 30 mm and more usually from about 5 to 20 mm, and has a width ranging from about 2 to 50 mm, usually from about 4 to 30 mm and more usually from about 5 to 20 mm. The substrate thickness may vary considerably, depending on the detection protocol, i.e. whether detection is through the substrate or just on the surface. For example, where the array is to be read through the substrate, the thickness generally ranges from about 0.7 to 1.2 mm. Alternatively, where the array is to be surface read, the thickness is generally dictated by the substrate fabrication process.

In the first embodiment of the subject invention mentioned above, the substrate employed in the subject methods is a substrate that has a plurality of distinct, individually controllable resistors associated with at least one of its surfaces, i.e. the surface on which it is desired to place one or more polymeric compounds. More particularly, the substrate in this first embodiment is generally made up of a base material having a plurality of resistors positioned on at least one surface thereof and then coated with an insulating layer that is modified, as necessary, to provide for any surface chemistry requisite for production of the polymer molecules on the substrate surface. The base material of the substrate is fabricated from any convenient material or materials, where the substrate may be a pure material or a composite structure of two or more different materials. As indicated above, the substrate can be fabricated from any material on which a plurality of resistors can be surface mounted.

Suitable materials therefore include silicon, fused glass, silica, and the like. Ideally, the substrate will have a surface that provided at most low background fluorescence.

On at least one surface of the base material, generally the planar surface of the base material, are a plurality of individually activatable resistors. By plurality is meant at least 2, usually at least 10 and more usually at least 100, where the number of resistors present on the substrate surface-may be as high as 100,000 or higher, but generally does not exceed about 20,000 and usually does not exceed about 10,000.

The resistors are generally positioned on the planar surface of the base material in the form of a pattern. Where the resistors are positioned on the base material in the form of a pattern, the pattern may vary as desired. As such, the pattern may be in the form of organized rows and columns of resistors, e.g. a grid of resistors, across the base material surface, a series of curvilinear rows across the substrate surface, e.g. a series of concentric circles or semi-circles of resistors, and the like.

The spacing of the resistors on the base material surface is sufficient to provide a density of at least about $1000/cm^2$, usually at least about $2000/cm^2$ and more usually at least about $2500/cm^2$, where the density may be as great as $40,000/cm^2$ or greater, but generally does not exceed about $10,000/cm^2$ and usually does not exceed about $4,000/cm^2$. In many embodiments the distance between any two given resistors on a base material surface is at least about 50 µm, usually at least about 100 µm and more usually at least about 160 µm, where the distance between any two adjacent resistors on the base material surface may be as great as 1 mm or greater, but generally does not exceed about 0.5 mm and usually does not exceed about 0.3 mm.

The resistors may be fabricated from any convenient material that is capable of undergoing a sufficient rise in temperature following application of an appropriate electrical current. As such, any material that is capable of achieving a temperature of at least about 50° C., usually at least about 90° C. and more usually at least about 110° C. upon application of an electrical current having a magnitude of from about 1 to 100 mA, usually from about 10 to 50 mA, may be employed. Suitable materials from which the resistors may be fabricated include: tantalum nitride, tantalum aluminum alloy, and the like.

Each of the resistors is individually activatable. By individually activatable is meant that the temperature of each resistor may be raised or lowered separately from any other resistor present on the substrate. As such, means for providing the requisite electrical current to each resistor are present on the base material surface, where such means may be any current communication means, such as stripes of a conducting material, etc. The means for applying electrical current to each resistor further includes a means for controlling which resistors are activated and which are not, i.e. a switching means for directing electrical current to the appropriate resistors associated with the substrate surface. A variety of suitable means as described above are known in the integrated circuit art and may be employed.

Positioned over the surface of the resistors on the base material is an insulating material, i.e. an insulator layer. The insulator material may be any convenient, nonconductive material or a composite of two or more inert materials, where suitable inert materials include silicon dioxide, silicon nitride, silicon carbide and the like, with silicon dioxide being preferred, with the only proviso being that the surface of the insulator layer must be susceptible to modification such that attachment of polymers to the surface can be achieved during polymer synthesis. The thickness of the insulator layer is typically at least about 0.1 and more usually at least about 0.2 µm, where the insulator layer may have a thickness as great as 2.0 µm or greater, but will generally not exceed about 1.5 µm and usually will not exceed about 1.0 µm. As such, the plurality of the resistors is associated with the substrate surface, and more specifically is beneath the substrate surface, i.e. underneath the insulating layer of the substrate.

The surface of the insulator layer is generally modified to provide for surface groups that allow for covalent attachment of the polymeric subunits onto the insulator layer during fabrication of the arrays. Surface reactive groups that may be introduced onto the surface of the insulating layer include: amino, e.g. primary amino; hydroxyl; thiol; sulfonic acid; phosphorous and phosphoric acid, particularly in the form of acid halides; especially chloride and bromide; and the like. The reactive groups may introduced onto the surface of the substrate using any convenient protocol, such as the protocols described in U.S. patent application Ser. No. 09/145,015 filed Sep. 1, 1998, the disclosure of which is herein incorporated by reference.

The above substrates may be fabricated using any convenient protocol, where standard IC fabrication and surface chemistry modification protocols are generally employed. A representative protocol is as follows is provided in the experimental section infra.

In the second embodiment, the substrate is not limited as in the first embodiment, in that the substrate employed in the second embodiment does not include a plurality of resistors. Instead, the bubble producing means, e.g. resistors, are present on a structure separate from the substrate, as summarized above. As such, the substrate may be any convenient substrate that finds use in biopolymeric arrays. In general, the substrate is rigid substrate in this second embodiment. By rigid is meant that the support is solid and does not readily bend, i.e. the support is not flexible. As such, rigid substrates are sufficient to provide physical support and structure to the nucleic acid spots present thereon. Furthermore, when the rigid supports of the subject invention are bent, they are prone to breakage. The substrates may be fabricated from a variety of materials. In certain embodiments, e.g. where one is interested in the production of nucleic acid arrays for use in research and related applications, the materials from which the substrate may be fabricated should ideally exhibit a low level of non-specific binding during hybridization events. In many situations, it will also be preferable to employ a material that is transparent to visible and/or UV light. For rigid substrates, specific materials of interest include: silicon; glass; plastics, e.g. polytetrafluoroethylene, polypropylene, polystyrene, polycarbonate, and blends thereof, and the like; metals, e.g. gold, platinum, and the like; etc. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, conformal silica or glass coatings, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g. conjugated. The particular surface chemistry will be dictated, as in the first embodiment, by the specific process to be used in polymer synthesis, as described in greater detail infra.

Turning now to the subject methods for producing arrays, the first step of the subject methods is to produce a solvent layer on at least one surface of the array, i.e. the surface on which the polymers are to be synthesized. The solvent layer may be produced on the surface of the substrate by any convenient protocol, such as by immersing the substrate in a container of the solvent, flooding the surface of the array with the solvent and the like. As such, the thickness of the solvent layer may vary widely, as long as it is sufficiently thick to provide for a suitable environment for the polymeric production chemistry to occur on the substrate surface coated with the solvent layer. In other words, the solvent layer must be of sufficient thickness to provide a suitable fluid environment for the polymeric synthesis chemical reactions to occur. Where the surface of the substrate is flooded with the solvent layer, the thickness of the solvent layer is generally at least about 100 $\mu$m, usually at least about 1 mm thick, where the thickness may be as great as 3 mm or greater, but generally does not exceed about 2.5 mm and usually does not exceed about 2 mm.

The solvent of the solvent layer is generally selected based on the particular chemistry to be performed in production of the polymeric binding agents. As such, depending on the particular chemical reactions to be performed during the synthesis of the polymers on the substrate surface, the solvent layer may be aqueous or nonaqueous. For example, the solvent layer may be aqueous in those situations where the solid phase polymeric synthesis protocols do not require anhydrous conditions. Aqueous solvents of interest include pure water, a water in combination with a cosolvent, e.g. an organic co-solvent, and the like. Where anhydrous conditions are required, e.g. in nucleic acid synthesis, non-aqueous solvents are employed. Nonaqueous solvents of interest include organic solvents, such as tetrahydrofuran, acetonitrile, dichloromethane, and the like, where acetonitrile is preferred in many embodiments, e.g. in the production of nucleic acid arrays.

Following production of the solvent layer on the substrate surface, the substrate surface is selectively protected. By "selectively protected" is meant that a portion of, but not all of, the potential reactive sites on the substrate surface (i.e. the sites containing covalently bound susceptible reactive moieties) are protected from reaction. As such, following selective protection of the substrate surface, only a portion of the potential susceptible reactive groups present on the substrate surface are actually available for reaction with a corresponding reactive group, i.e. a group that reacts with the surface bound susceptible moiety.

The substrate surface is selectively protected with one or more protective bubbles positioned on the surface at sites where prevention of reaction between surface bound susceptible groups and reactive agents in the solvent layer is desired. The protective gas bubbles are produced at a desired site(s) on the substrate surface to achieve selective protection of the substrate surface in any convenient manner.

In the first embodiment of the subject invention (i.e. where the substrate comprises a plurality of individually activatable resistors), selective protection of one or more sites is achieved by activating the resistor associated with the substrate surface at each site where protection is desired, i.e. by selectively activating the resistors associated with the substrate surface. In selectively activating the resistors associated with the substrate surface, only a portion of the total number of resistors is activated, where the portion that are activated are those that underlie the surface at the site at which protection is desired.

In the second embodiment of the subject invention, as summarized above the resistors (or other bubble producing means) are present on a structure that is separate from the substrate. Typically, though not necessarily, the resistors are present on a plate like structure of analogous proportions and composition to the substrate of the first embodiment (with the exception that the surface need not be modified to provide for functional groups employed in the polymer synthesis protocol), such that the resistors can be lined up with discrete and known locations of the substrate to protect these locations at various stages during the synthesis. In these embodiments, the structure comprising the resistors is brought within sufficiently close proximity to the substrate surface such that the bubble which nucleates on the separate structure is capable of touching and covering a reactive site on the substrate.

The resistors (present on either the substrate or the separate structure, as described above) are selectively activated by applying an electrical current to those resistors located at the site of either the substrate surface to be protected or on the separate structure immediately opposite the substrate surface location to be protected. The surface area of the substrate covered by each bubble, i.e. the surface area of the substrate at which solvent is prevented from having contact with the susceptible moieties stably attached thereto, generally ranges from about 100 to 62,500 $\mu$m$^2$, usually from about 625 to 22500 $\mu$m$^2$, and more usually from about 2500 to 10,000 $\mu$m$^2$. The electrical current applied to the resistor in the production of the protective bubble is sufficient to raise the temperature of resistor such that a protective bubble of desired volume is produced, where the temperature of the resistor varies depending on the nature of the solvent layer.

Following selective protection of the substrate surface, the selectively protected surface is contacted with a reactive agent that is capable of reacting with unprotected susceptible groups on the substrate surface. Contact may be achieved by any convenient means. Typically, the reactive agent is introduced into the solvent layer on the surface of the substrate in a manner that does not disrupt the protective bubble(s). Contact is maintained for a sufficient period of time and under sufficient conditions for the reactive agent to react with substantially all of the unprotected susceptible moieties present on the substrate surface. This incubation period varies depending on the nature of the reaction being performed, but generally lasts for a period of time ranging from about 5 sec to 10 min, usually from about 10 sec to 5 min and more usually from about 10 sec to 1 min. Contact of the selectively protected substrate surface with the reactive agent results in the surface modification of a portion of, but not all of, the substrate surface. In other words, the portion of the substrate surface not selectively protected by the protective bubble(s) is chemically modified, e.g. by the addition of a monomeric residue or by the removal of a protective group depending on whether the reactive agent is an activated monomer or a deblocking agent, following contact with the reactive agent.

Following contact of the substrate layer with the reactive agent and the passage of a sufficient period of time for all potential reactions between the reactive agent and unprotected susceptible moieties present on the substrate surface to occur, any remaining reactive agent (i.e. un-reactive reactive agent) is removed from the substrate surface. Removal of the un-reacted agent from substrate surface may be accomplished using any convenient methodology. Thus, one may use washing protocols to remove the un-reacted reactive agent. Washing protocols may involve replacing the solvent layer present on the substrate surface with a fresh solvent layer, flooding the substrate surface with fresh solvent so to displace essentially all of the prior solvent, and the like. During or after the washing procedure, depending on the particular protocol employed, the selective activated resistors are deactivated. As such, following the washing procedure, one obtains a substrate surface that has been selectively modified, e.g. protective groups removed or polymeric subunit covalently attached, in those areas that were not protected by the protective bubbles.

Following washing, the entire substrate surface is contacted with the next reactive agent in the polymeric synthesis protocol, e.g. an activated monomer such as a nucleotide where the initial reactive agent contacted with the selectively protected substrate surface is a deblocking agent; or a deblocking agent such as dichloroacetic acid or trichloroacetic acid where the initial reactive agent is an activated nucleotide. Contact between this second reactive agent and the substrate surface is maintained for a period of time sufficient for any potential reactions to occur between this second reactive agent and susceptible moieties on the substrate surface. As in the first step, un-reacted reactive agent is then removed from the substrate surface following this incubation step, e.g. by washing.

By reiterating or repeating the above synthesis steps of selective protection, reagent contact with the selectively protected surface, washing, and reagent contact with entire surface (which is not selectively protected), polymeric compounds are grown at various positions on the surface of the substrate. By controlling the nature of the reactive agents and the selective protection of the surface, an array of diverse polymeric compounds may be synthesized on the substrate surface.

As mentioned above, the subject invention can be used to produce a number of different types of arrays, including nucleic acid and peptide arrays. A preferred embodiment of the subject invention is the use of the subject methods to produce nucleic acid arrays. Nucleic acid arrays are produced according to the subject invention by synthesizing nucleic acid polymers using conventional phosphoramidite solid phase nucleic acid synthesis chemistry where the solid support is a substrate as described above and protective bubbles are employed at various stages of the step-wise synthesis procedure to selectively protect certain sites on the substrate surface from reaction during the synthesis protocol. Phosphoramidite based chemical synthesis of nucleic acids is well known to those of skill in the art, being reviewed in Streyer, Biochemistry (1988) pp 123–124 and U.S. Pat. No. 4,415,732, the disclosure of the latter being herein incorporated by reference.

To produce nucleic acid arrays according to the subject methods, a substrate surface as described above having the appropriate surface groups, e.g. —OH groups, present on its surface, is obtained. See the Experimental Section infra for a representative protocol for preparing such a substrate. Since the synthesis protocol must be carried out under anhydrous conditions, all reactions are carried out in a nonaqueous, typically organic solvent layer on the substrate surface, where the solvent layer is acetonitrile in many embodiments.

Next, the first residues of each nucleic acid to be synthesized on the array are covalently attached to the substrate surface via the surface bound —OH groups. Depending on whether the first nucleotide residue of each nucleic acid to be synthesized on the array is the same or different, different protocols for this step may be followed. Where each of the nucleic acids to be synthesized on the substrate surface have the same initial nucleotide at the 3' end, the entire surface of the substrate is contacted with the appropriate activated nucleoside under conditions sufficient for coupling of the activated nucleoside to the reactive groups, e.g. —OH groups, present on the substrate surface to occur. Alternatively, where the initial residue of the various nucleic acids differs among the nucleic acids, one or more sites on the substrate surface are initially selectively protected with protective bubbles, as described supra, by activating the appropriate resistors (either in the substrate or the structure separate from the substrate, as described above). Following selective protection of the surface, the appropriate activated nucleotide, e.g. A, is then contacted with the substrate surface. Next, different sites on the substrate surface are selectively protected, followed by contact with a different activated nucleotide, e.g. C. This process is then repeated with additional different activated nucleotides, e.g. T & G, until all of the initial nucleotides of each to be synthesized nucleic acids are deposited on the substrate surface. At some point during this initial deposition, usually following deposition of all of the initial nucleotides, phosphite triesters present on the substrate surface following coupling are converted to phosphotriesters, e.g. by oxidation with a suitable oxidating agent, such as $I_2/H_2O$. In addition, unreacted hydroxyl groups are usually (though not necessarily) capped, e.g. using any convenient capping agent, as is known in the art.

Following covalent attachment of the initial nucleotides of each nucleic acid, the following two steps are performed: (1) selectively protecting one or more positions on the substrate surface with protective bubbles; and (2) contacting the selectively protected surface with a reactive agent, where the reactive agent may be a deblocking agent or an activated nucleotide. Since the protocols vary depending on whether the reactive agent contacted with the selectively protected surface is a deblocking agent or an activated nucleoside phosphoramidite, each of these situations is described separately below.

Where the reactive agent contacted with the selectively protected substrate surface is a deblocking agent, the first step following production of the substrate having the first monomeric residue of each nucleic acid on its surface is to selectively protect one or more positions on the substrate surface with protective bubble(s). Selective protection results in a portion of the sites on the substrate surface being exposed to the solvent layer and a portion of the sites on the substrate surface being "hidden" from the solvent layer. The selectively protected substrate surface is then contacted with a deblocking or deprotecting agent, e.g. by introducing a deblocking agent into the solvent layer. Following introduction of the deblocking agent, the substrate surface is incubated for a sufficient period of time under appropriate conditions for all available protecting groups, e.g. all protecting groups not protected, i.e. underneath, a protective bubble, to be cleaved from the nucleotides that they are protecting.

Contact of the selectively protected substrate surface with a deblocking agent results in removal of the protecting groups from those substrate bound residues not underneath a protective bubble. As such, this step results in the deprotection of a portion of the nucleotide residues on the substrate surface. Following deprotection, the deblocking agent is removed from the solvent layer on the surface of the substrate, where removal of the deblocking agent can be accomplished using any convenient protocol. Thus, the solvent layer may be completely removed from the substrate surface, and then replaced with fresh solvent layer, following one or more washing steps. Alternatively, a sufficient amount of the solvent layer may be replaced with new solvent in a flow through protocol in a manner sufficient to reduce the concentration of deblocking agent present above the substrate surface to essentially zero, e.g. by flushing the substrate surface with fresh solvent. Either during or after this washing step, the protective bubbles are removed, e.g. by deactivating the selectively activated resistors on either the substrate or the structure separate from the substrate, depending on which embodiment of the invention is being employed.

Removal of the deblocking agent and protective bubbles results in a substrate surface in which a portion of the bound nucleotide residues are deprotected and a portion of the bound nucleotide residues are protected. In others words, removal of the protective bubbles and deblocking agent results in the production of an array of nucleotide residues stably associated with the substrate surface, where a portion of the nucleotide residues on the array surface have —OH groups available for reaction with an activated nucleotide.

The next step in the subject methods is to contact this selectively deprotected array of surface bound nucleotides with an activated nucleotide under conditions sufficient for coupling between the activated nucleotide and the deprotected surface bound nucleotide to occur. Contact of the selectively protected surface with the activated nucleotide may be accomplished using any convenient protocol, e.g. by contacting the surface with a solution of the activated monomer; introducing the activated monomer into a solvent layer already present on the substrate surface; and the like. Contact of the selectively protected surface with the activated nucleotide is maintained for a sufficient period of time for coupling to occur. Coupling results in the production of a substrate having a surface in which a portion of the surface bound nulceic acids have been elongated by one nucleotide residue, while the remainder have not. Next, unbound activated nucleotide is removed from the surface, e.g. by washing. As is known in the art, at some convenient point during the above steps, e.g. after each coupling or after all of the couplings of a given layer, the phosphite triesters that result from coupling are oxidized to phosphotriesters. The only limitation on this oxidization step is that it generally occurs prior to the addition of the next nucleotide residue on a growing chain.

The above steps of: (a) selective protection; (b) contact of the selectively protected surface with a deblocking agent; and (c) contact of the entire surface with an activated nucleotide are repeated with additional nucleotides until each of the desired nucleic acids on the substrate surface are produced. By choosing which sites are protected at each selective protection step as well as which activated nucleotides, e.g. A, G, C & T, are contacted with the entire substrate surface, an array having polymers of desire sequence and spatial location is readily achieved.

The above protocol varies somewhat where the reactive agent that is contacted with the selectively protected surface is the activated nucleotide. In this embodiment, the first step in the synthesis of the nucleic acids, following stable attachment of the terminal nucleotides to the substrate surface, is to deblock all of the nucleotides on the substrate surface, e.g. to contact the entire surface with a deblocking agent. Following contact of the entire surface with a deblocking agent, the surface is selectively protected as described above, which results in a portion of the deblocked substrate bound nucleotides being "hidden" underneath protective bubbles. The selectively protected substrate surface is then contacted with an activated nucleotide under coupling conditions, whereby elongation occurs at those sites on the substrate surface not under a protective bubble. Following elongation, remaining activated nucleotide is removed e.g. by washing. The surface is then selectively protected at different locations, where at least a portion of the sites initially protected remain unprotected by a protective bubble, and all of the unprotected sites in the first activated nucleotide contact step are generally (though not necessarily) protected (reaction should not occur at these sites since they are occupied by the first activated monomer which is protected). This second selectively protected substrate surface is contacted with a second activated monomer to elongate the nucleic acid present at the unprotected sites. By reiterating these steps with the remaining activated monomers, each of the nucleic acids on the array is elongated by one residue. Thus, this protocol is analogous to the first protocol, with the only difference being that the activated monomer is contacted with the selectively protected surface and the deblocking agent is contacted with the entire surface. As with the first protocol, by tailoring the selective protection and the sequence of activated nucleotide contact, one can obtain a nucleic acid array of any desired sequence and spatial characteristics.

As mentioned above, the subject methods (particularly of the second embodiment) are also amenable to the production of peptide arrays, i.e. arrays of polymeric agents which are characterized by the presence of peptide bonds. Any convenient solid phase peptide synthesis protocol may adapted to practice the subject methods, where the resistor comprising substrates of the subject methods are employed as the solid phase. Jones, The Chemical Synthesis of Peptides (Oxford University Press)(1993) provides a review of solid phase peptide synthesis. The preparation of peptides according to the subject methods is analogous to the preparation of nucleic acids described above. Thus, the reactive agent contacted with selectively protected surface may be a deprotecting agent or an $\alpha$-amino protected amino acid. Where the reactive agent contacted with the selectively protected surface is a deblocking or deprotecting agent, the method further includes contacting the entire surface of the substrate with an $\alpha$-amino protected amino acid. Conversely, where the reactive agent that is contacted with the selectively protected surface is an $\alpha$-amino protected amino acid, the deblocking agent is contacted with the entire surface. As with the nucleic acid synthesis, by appropriate selection of which sites to selectively protect at a give time and the order of contact of the $\alpha$-amino protected amino acids with the substrate surface, a peptide array of any desired spatial and sequence characteristics may be obtained.

The subject methods result in the production of arrays of polymeric binding agents, e.g. nucleic acid arrays, peptide arrays, etc. The density and overall number of the polymeric binding agents on the substrate surface may vary greatly. Because of the methods by which the subject arrays are produced, the length of each polymer on the substrate surface of the arrays generally does not exceed about 50 monomeric units, usually does not exceed about 35 monomeric units and more usually does not exceed about 25 monomeric units. In those arrays produced according to the first embodiment of the subject invention, described above, a plurality of resistors are associated with the surface of the substrate to which the polymeric binding agents are stably attached.

The subject arrays find use in a variety applications, where such applications are generally analyte detection applications in which the presence of a particular in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like.

Where the subject arrays are arrays having a plurality of resistors incorporated into the substrate, e.g. such as those produced according to the first embodiment of the subject invention, assays can be performed in which one or more of the resistors is selectively activated to modulate the temperature of the reaction solution above the substrate surface, e.g. during hybridization or detection. For example, the resistors could be heated to different temperatures to get the desired stringency for each probe type during a nucleic acid hybridization reaction. Alternatively, for polymorphism analysis, melt-off experiments may be performed. In such experiments, the hybridization is allowed to proceed and then the array is scanned wet. Then each resistor is slowly heated while the array is rescanned. As the probe/target pairs are heated, they will separate and the signal at each feature will drop. The signal is plotted relative to temperature (or voltage applied to the resistor). The point of inflection on the curve is called $T_m$ or the melting point of the probe/target hybridization. At this point, half of the probe/target pairs have separated. $T_m$ gives a measure of the binding strength of the hybridization. Exact compliments have higher $T_m$'s than pairs with mismatches such as single base changes, additions or deletions.

Also provided by the subject invention are kits for use in producing the subject arrays. Kits for producing the subject arrays generally include at least a substrate having a plurality of individually activatable resistors associated with a surface thereof. The kits may further include various reagents that are employed in the polymeric synthesis protocol, e.g. deblocking agent, monomers, e.g. DMT protected nucleotide phosphoramidites, activating agents, solvents, oxidizing agents, and the like. In addition, the kits typically further include instructions for how to synthesize a polymeric array according to the subject methods, where these instructions are generally present on at least one of a package insert and the package of the kit.

Finally, kits for use in analyte detection assays are provided. The subject kits at least include the arrays of the subject invention. The kits may further include one or more additional components necessary for carrying out the analyte detection assay, such as sample preparation reagents, buffers, labels, and the like. In addition, the kits typically further include instructions for how practice the subject analyte detection methods according to the subject invention, where these instructions are generally present on at least one of a package insert and the package of the kit.

The following examples are offered by way of illustration and not by way of limitation.

Experimental

I. Preparation of a Resistor Substrate for Use in the Synthesis of Nucleic Acid Arrays A resistor substrate is prepared according to the method described in U.S. Pat. No. 4,809,428, the disclosure of which is herein incorporated by reference, with the only difference being that the barrier layer is not applied. Instead another coating of $SiO_2$ is applied in thickness ranging from about 0.25–1 micron. The surface of then functionalized according to the process disclosed in U.S. patent application Ser. No. 09/145,015, filed Sep. 1, 1998, the disclosure of which is herein incorporated by reference, to provide for surface —OH groups.

II. Production of Nucleic Acid Arrays.

Nucleic acid arrays are synthesized on the functionalized surface of resistor substrates, as described above, according to the following methods.

A. Protecting at the Phosphoramidite Addition Step.

The substrate is built as described in Section I above through the addition of the two passivation layers, where the $SiO_2$ layer is added only in the region of the resistors. As such, the addition of the linker chemistry only occurs on the $SiO_2$ layer. The linker chemistry does not have any protecting group and ends in a hydroxyl, thereby providing the requisite surface —OH moieties required for synthesis of the nucleic acids.

The surface is flooded in acetonitrile. Bubbles are formed over the features that will not couple the first phosphoramidite. The acetonitrile is exchanged with acetonitrile that contains the first phosphoranidite. The coupling reaction occurs. The phosphoramidite solution is removed by exchange with neat acetonitrile. The resistors are turned off. Any remaining bubbles are washed off by the capping solutions that flood the surface. The process is repeated for the three remaining phosphoramidites such that all of the sites have a first base coupled. After the last coupling, the surface is flooded with the oxidizing reagents (capping if employed) and then the deblocking reagents. The process is repeated for the second round of base additions.

B. Protecting at the Deblock Step.

In this embodiment, the surface of the resistor substrate as describe in Section I above is modified such that the surface linker includes a protecting group, such as dimethyloxytrityl. It is assumed that the active surface covers the entire surface, the area over the resistors and the area between the resistors. The first step is to inactivate the area between the resistors. The surface is flooded with dichloromethane. Bubbles are formed at all of the resistor locations. The solvent is exchanged with 3% dichloroacetic acid or trichloroacetic acid in dichloromethane to deblock the non-resistor surfaces. The solvent is exchanged with dichloromethane and the resistors are turned off. The surface is flooded with the capping reagents to cap all the hydroxyls between the features. The synthesis process can now start. The surface is again flooded with dichloromethane. Bubbles are formed at those resistor locations that will not be receiving the first phosphoramidite. The solvent is exchanged with 3% trichloroacetic acid in dichloromethane to deblock those sites that will receive the first phosphoramidite. Again the solvent is exchanged with dichloromethane and the resistors are turned off. The dichloromethane is removed and the surface is flooded with the first phosphoramidite. It can couple only at the sites that were deprotected. The phosphoramidite is removed and the surface is flooded with the capping solutions. These solutions are removed and the surface is flooded with the oxidation reagents. These reagents are removed and the process is started again. The next set of features is deprotected and the second phosphoramidite is added. Normally, the process must be repeated four times to get a single base addition at each location. The process is repeated until oligos of the desired length are built at each feature.

The resultant nucleic acid arrays find use in variety of hybridization applications, as describe supra.

It is evident from the above results and discussion that a simple and efficient way to prepare polymeric arrays is provided. Because the substrate is selectively protected by protective bubbles at appropriate stages during the polymeric synthesis process, all of the steps in the synthesis process are alignment independent, which is a distinct advantage over prior art methods, particularly those in which large numbers of distinct polymers are to be positioned on the substrate surface. Furthermore, the subject methods are readily adaptable to automated systems. As such, the subject invention is a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A composition comprising:

a plurality of distinct polymers stably associated with the surface of a substrate, wherein said substrate comprises a plurality of individually activatable resistors associated with said surface, and at least one of said polymers is associated with at least one of said resistors; and a solvent layer present on said surface, wherein a portion of said substrate surface is selectively protected from reactive agents in said solvent layer by a protective gas bubble.

2. The composition according to claim 1, wherein said plurality of resistors are beneath said surface of said substrate.

3. A composition comprising:

a plurality of nucleic acid spots stably associated with the surface of a substrate, wherein said substrate comprises a plurality of individually activatable resistors beneath said surface and at least one of said nucleic acid spots is associated with at least one of said resistors; and a solvent layer present on said surface, wherein a portion of said substrate surface is selectively protected from reactive agents in said solvent layer by a protective gas bubble.

4. The composition according to claim 1, wherein said polymers are nucleic acids.

5. The composition according to claim 1, further comprising an electrical current application means associated with said resistors.

6. The composition according to claim 5, further comprising an electrical current controlling means associated with said electrical current application means.

7. The composition according to claim 3, further comprising an electrical current application means associated with said resistors.

8. The composition according to claim 7, further comprising an electrical current controlling means associated with said electrical current application means.

* * * * *